(12) United States Patent
Shimazaki et al.

(10) Patent No.: US 7,727,203 B2
(45) Date of Patent: Jun. 1, 2010

(54) COMBINED CONTAINER-SYRINGE

(75) Inventors: Seiji Shimazaki, Takahagi (JP); Makoto Kakiuchi, Takahagi (JP)

(73) Assignee: Arte Corporation, Tokyo (JP)

( * ) Notice: Subject to any disclaimer, the term of this patent is extended or adjusted under 35 U.S.C. 154(b) by 711 days.

(21) Appl. No.: 11/337,056

(22) Filed: Jan. 19, 2006

(65) Prior Publication Data
US 2006/0184138 A1 Aug. 17, 2006

(30) Foreign Application Priority Data
Jan. 20, 2005 (JP) .............................. 2005-012579

(51) Int. Cl.
*A61M 5/00* (2006.01)
(52) U.S. Cl. ..................................... 604/240
(58) Field of Classification Search ............. 604/232, 604/240, 187
See application file for complete search history.

(56) References Cited

U.S. PATENT DOCUMENTS

| | | | |
|---|---|---|---|
| 3,967,759 A | 7/1976 | Baldwin et al. | |
| 4,048,997 A | 9/1977 | Raghavachari et al. | |
| 4,235,235 A * | 11/1980 | Bekkering ................... | 604/238 |
| 4,342,724 A * | 8/1982 | Narra .......................... | 422/101 |
| 4,529,403 A * | 7/1985 | Kamstra ..................... | 604/136 |
| 4,976,693 A | 12/1990 | Haast | |
| 5,364,369 A * | 11/1994 | Reynolds ..................... | 604/187 |
| 5,380,286 A | 1/1995 | van den Haak | |
| 5,779,683 A * | 7/1998 | Meyer ......................... | 604/198 |
| 5,971,953 A * | 10/1999 | Bachynsky ................... | 604/90 |
| 6,004,299 A * | 12/1999 | Arai et al. .................... | 604/218 |
| 6,027,481 A * | 2/2000 | Barrelle et al. .............. | 604/187 |
| 6,966,897 B2 * | 11/2005 | Shimazaki .................... | 604/189 |
| 2002/0045858 A1 | 4/2002 | Alchas et al. | |
| 2002/0052577 A1* | 5/2002 | Shimazaki ................... | 604/192 |
| 2004/0168293 A1* | 9/2004 | Shimazaki ..................... | 29/456 |
| 2008/0091148 A1* | 4/2008 | Shimazaki et al. .......... | 604/218 |

FOREIGN PATENT DOCUMENTS

| | | |
|---|---|---|
| EP | 0581454 | 2/1994 |
| FR | 2208684 | 6/1974 |

(Continued)

OTHER PUBLICATIONS

European Search Report dated Apr. 20, 2006 for European Application No. EP06100611.
Letter with date of receipt stamped Jun. 8, 2006 from DeVries & Metman to Shiga International Patent Office.

(Continued)

*Primary Examiner*—Nicholas D Lucchesi
*Assistant Examiner*—Aarti B Berdichevsky
(74) *Attorney, Agent, or Firm*—Kolisch Hartwell, PC (57) ABSTRACT

This combined container-syringe comprising a glass cylinder which can be pre-filled with a drug, an cylindrical tip provided at an exterior portion of an anterior end of the syringe, and a finger grip provided at an exterior portion of an posterior end of the syringe, and a drug is pre-filled therein and sealed by a stopper. Furthermore, an impact absorption part is provided around the exterior portion of the cylindrical tip and a diameter of the impact absorption part is greater than an outer diameter of a fitting part to the cylinder of the cylindrical tip.

5 Claims, 5 Drawing Sheets

FOREIGN PATENT DOCUMENTS

| | | |
|---|---|---|
| JP | 08-141081 | 6/1996 |
| JP | 08-141091 | 6/1996 |
| JP | 2002-177393 | 6/2002 |
| WO | WO00/07646 | 2/2000 |
| WO | WO01/30424 | 5/2001 |

OTHER PUBLICATIONS

Japanese Office Action from corresponding Japanese Application No. 2005-12579, mailed on May 27, 2008.

Office Action from corresponding Japanese Application No. 2005-012579, dated Sep. 30, 2008.

* cited by examiner

100
COMBINED CONTAINER-SYRINGE

BACKGROUND OF THE INVENTION

1. Field of the Invention

The present invention relates to a combined container-syringe which can be pre-filled with a drug, stored, and immediately used after removal from the package at the time of usage. Priority is claimed on Japanese Patent Application No. 2005-012579 filed on Jan. 20, 2005, the content of which is incorporated herein by reference.

2. Description of the Related Art

A combined container-syringe comprising a glass cylinder, a cylindrical tip fitted at an anterior end of the glass cylinder, a finger grip provided at a posterior end of the glass cylinder, and a drug pre-filled and sealed in the cylinder by a stopper, is well known. This kind of syringe is disclosed by Japanese Unexamined Patent Application, First Publication Nos. H08-141081 and H08-141091, for example. However, in this combined container-syringe comprising the glass cylinder pre-filled with a drug and packaged by pharmaceutical companies, when impactive stress is applied onto an exterior of the syringe pre-filled with the drug and packaged during a distribution process from the pharmaceutical companies to medical institutions or at the time of usage, tiny crack may be formed rarely on the anterior end of the cylinder where the cylindrical tip is fitted. Such accidents cannot be occurred by ordinary handling because the combined container-syringe has enough strength against the stress applied onto the exterior of syringe and packaging for combined container-syringe has enough protection properties against the stress during distribution processes. However, when the packaged syringe is dropped from unexpected height, or impact is applied to the syringe which is taken out from the packaging, the tiny crack may be rarely occurred on the anterior end portion of the cylinder where the cylindrical tip is fitted.

SUMMARY OF THE INVENTION

Considering above mentioned situation, the present invention provides a combined container-syringe in which the anterior end of the glass cylinder is prevented as much as possible from being cracked when the unexpected stress is applied onto the syringe.

In order to achieve the above-described purposes, the combined container-syringe of a first aspect of the present invention comprises a glass cylinder in which a drug is pre-filled and sealed therein by stoppers, a cylindrical tip provided at an exterior portion of an anterior end of the glass cylinder, a finger grip provided at an exterior portion of a posterior end of the glass cylinder, and an impact absorption part provided around an exterior portion of a fitting part to the cylinder of the cylindrical tip and the diameter of the impact absorption part is greater than the outer diameter of the fitting part of the cylindrical tip.

According to the combined container-syringe of the first aspect of the present invention, even if the combined container-syringe is dropped, the impact absorption part absorbs impact applied to the anterior end of the glass cylinder and reduces a deformation amount of a cross section of the glass cylinder to oval shape. As a result, the anterior end of the glass cylinder is prevented from being cracked as much as possible when unexpected stress is applied.

Furthermore, in the combined container-syringe of a second aspect of the present invention, the impact absorption part is a circular rib integrally formed around the exterior portion of the fitting part of the cylindrical tip along a direction perpendicular to an axis of the glass cylinder.

This circular rib absorbs the impact applied to the anterior end of the glass cylinder and effectively prevents it from being cracked when the combined container-syringe is dropped.

Furthermore, in the combined container-syringe of a third aspect of the present invention, the circular rib is provided at a posterior end of the fitting part of the cylindrical tip.

This circular rib directly prevents the impact applied to the anterior end of the glass cylinder when the combined container-syringe is dropped, and therefore, the anterior end of the glass cylinder can be more effectively prevented from forming of a crack.

Furthermore, in the combined container-syringe of a fourth aspect of the present invention, the impact absorption part is a cylindrical cover attached to the fitting part of the cylindrical tip and made of flexible plastics having shock absorption ability.

This cylindrical cover absorbs the impact applied to the anterior end of the glass cylinder efficiently, and therefore, the cylindrical cover prevents the forming of the crack more effectively at the anterior end of the glass cylinder.

Furthermore, in the combined container-syringe of a fifth aspect of the present invention, the impact absorption part is a cylindrical cover made of rigid plastics and placed around the outer surface of the fitting part with a predetermined clearance.

This cylindrical cover absorbs impact by deforming itself when the combined container-syringe is dropped, and therefore, the anterior end of the glass cylinder is more reliably prevented from being cracked.

Furthermore, in the combined container-syringe of a sixth aspect of the present invention, the cylindrical cover has circular flanges which project inward direction at two end portions of the fitting part. One of these flanges defines an aperture of which its inner surface can be fitted around an outer surface of a cylindrical part of the cylindrical tip, and the other flange having a tapered insertion hole. The diameter of the insertion hole is smaller than that of the outer surface of the fitting part at another flange side, and is greater than that of the outer surface of the fitting part at the side which is apart from another flange.

This cylindrical cover is easily installed with the fitting part through the tapered insertion hole, and also the flanges on the end portions of the cylindrical cover are reliably attached to the fitting part.

DETAILED DESCRIPTION OF THE INVENTION

Figure 1:
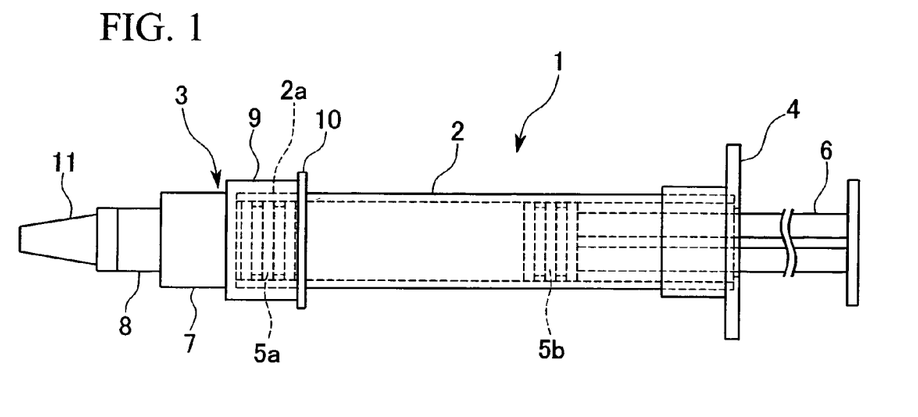
FIG. 1 is a side view of a combined container-syringe according to a first embodiment of the present invention.
Figure 2:
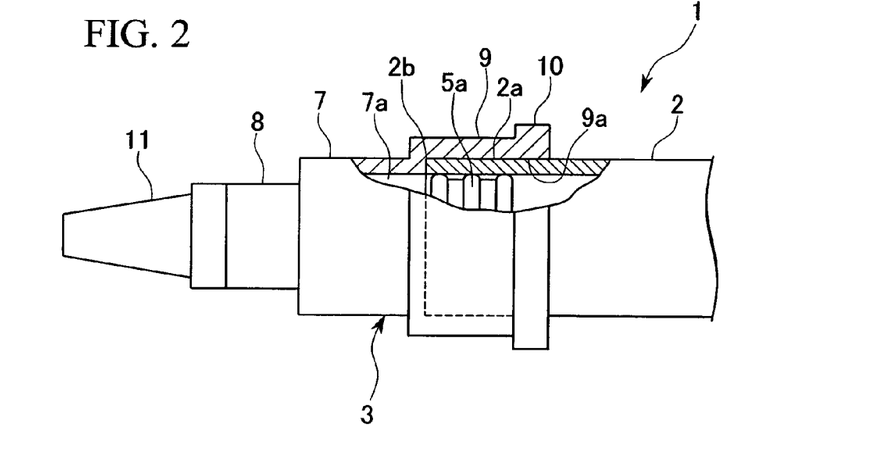
FIG. 2 is an enlarged side view of the combined container-syringe of FIG. 1 with a partial cross section thereof.

FIGS. 1 and 2 show a combined container-syringe 1 according to the first embodiment of the present invention.

The combined container-syringe 1 comprises a glass cylinder 2, a hub luer-lock type cylindrical tip 3 provided at the anterior end of the glass cylinder 2, a finger grip 4 made of plastics and provided at the posterior end of the glass cylinder 2, a front stopper 5a and an end stopper 5b inserted into the glass cylinder 2 so as to position at the front and rear ends of the glass cylinder 2 and can be move reciprocally along an axis of the glass cylinder 2 in order to seal a drug pre-filled in the glass cylinder 2, and a plunger rod 6 inserted into the glass cylinder 2 from the rear end and connected to the stopper 5b to move the stopper 5b reciprocally along the axis of the glass cylinder 2. The cylindrical tip 3 may be a luer-tip type instead of a hub luer-lock type. The cylindrical tip 3 is made of transparent plastics, and as shown in FIG. 2, the cylindrical tip 3 is composed of a cylindrical part 7 equipped with an inner chamber 7a for receiving the front stopper 5a with inner diameter same or slightly greater than that of the glass cylinder 2, a luer-locking member 8 equipped with an inner channel connecting to the inner chamber 7a and acting as a fitting member of an injection needle, and a cylindrical fitting part 9 integrally formed at the posterior end of the cylindrical part 7 with outer diameter greater than that of the cylindrical part. The cylindrical tip 3 is connected to the glass cylinder 2 by fitting an inner hole 9a of the fitting part 9 around an outer surface of the anterior end part 2a of the glass cylinder 2.

On exterior portion of the posterior end (posterior end along an axial direction of the glass cylinder 2) of the fitting part 9 of the aforementioned cylindrical tip 3, a single circular rib 10 (impact absorption part) is integrally formed along a direction perpendicular to the axis of the glass cylinder 2 so as to project outwardly along the radial direction of the glass cylinder 2. That is, the circular rib 10 is formed along a circumferential direction of the fitting part 9, and the outer diameter of the circular rib 10 is greater than that of the fitting part 9.

Although the size of the circular rib 10 can be adjusted in accordance with the external diameter of the glass cylinder 2, the height of the circular rib 10 is set from 0.5 mm to 5 mm higher than that of the cylindrical fitting part 9 (the diameter of the circular rib 10 is from 1.0 mm to 10 mm greater than that of the cylindrical fitting part 9), and the thickness of the circular rib along the axis of the glass cylinder 2 is set from 0.5 mm to 3.0 mm. When the size of the rib 10 is set within as mentioned above, external force applied to an anterior end 2b of the glass cylinder 2 induced by the impact during a handling of the combined container-syringe can be reduced, and the cylindrical tip 3 can be easily form without strange appearance of combined container-syringe and the circular rib 10 does not interfere the handling at the time of usage. If the size of the circular rib 10 toward the fitting part 9 is smaller than the above lower limit, the impact applied to the anterior end 2b of the glass cylinder 2 cannot be expected to reduce sufficiently, and if the size of the circular rib 10 toward the fitting part 9 is greater than the above higher limit, the appearance of the combined container-syringe looks strange and may occur problems for easy handling. Furthermore, a cap 11 attached to the luer-locking member 8 of the cylindrical tip 3 can seal an inside of the cylindrical tip 3 in an air and liquid tight condition until the injection needle is attached to the luer-locking member 8.

As mentioned above, by providing the circular rib 10 in the axial direction of the cylindrical tip 3 as the impact absorbing part at the outer circumference of the posterior end of the fitting part 9 of the cylindrical tip 3, if the packaged combined container-syringe 1 is roughly packed into a storage unit from a height or is fallen onto a table and the like from the storage unit in a distribution process or a handling in a medical institute, the fitting part 9 is bent to a horizontal direction at instant along the diameter direction and the cross section of the fitting part is elastically deformed to oval shape by a large impact force applied to the fitting part 9 of the cylindrical tip 3. However, since the deformation of the glass cylinder 2 or a cracking around the cylindrical tip of the glass cylinder can be reduced at as much as possible by buffering action and recovering action of the rib 10, the large deformation of the cylindrical tip 2b of the glass cylinder 2 to the oval shape and the stress applied to the both ends along the longitudinal direction of the oval at the cylindrical tip can prevented. Furthermore, by providing the circular rib 10 at the posterior end of the fitting part 9 in the axial direction of the glass cylinder 2, a direct impact to the anterior end 2b of the glass cylinder 2 could be prevented by receiving the impact by the aforementioned rib 10. From this point, a crack induced around the anterior end 2b of the glass cylinder 2 can be prevented by reducing a stress applied to the anterior end 2b of the glass cylinder 2.

In addition, even if the combined container-syringe 1 having a crack induced around the anterior end 2b of the glass cylinder 2, the combined container-syringe 1 is not used carelessly, since the presence of the crack in the aforementioned cylinder 2 can be easily distinguished before usage because of the aforementioned cylindrical tip is composed of transparent materials.

In the above described combined container-syringe 1, a single circular rib 10 as the impact absorption part is provided only in the axial direction of the cylindrical tip on the posterior end of the fitting part 9 of the cylindrical tip 3, however, the position and number of ribs are not limited to the above, and the rib provided at a different position with different number may be selected. For example, in FIG. 3 which shows a combined container-syringe 1A according to the second embodiment of the present invention, a single circular rib 10a (the impact absorption part) is formed integrally in the direction perpendicular to the axis of the glass cylinder 2 at the anterior end of the fitting part 9 of the cylindrical tip 3. Furthermore, in FIG. 4 which shows a combined container-syringe 1B according to the third embodiment of the present invention, the circular rib 10a is provided around the exterior portion of the anterior end of the aforementioned cylindrical part 7. The height (outer diameter) and the thickness of the circular rib 10a are as same as those of the aforementioned circular rib 10.

Figure 3:
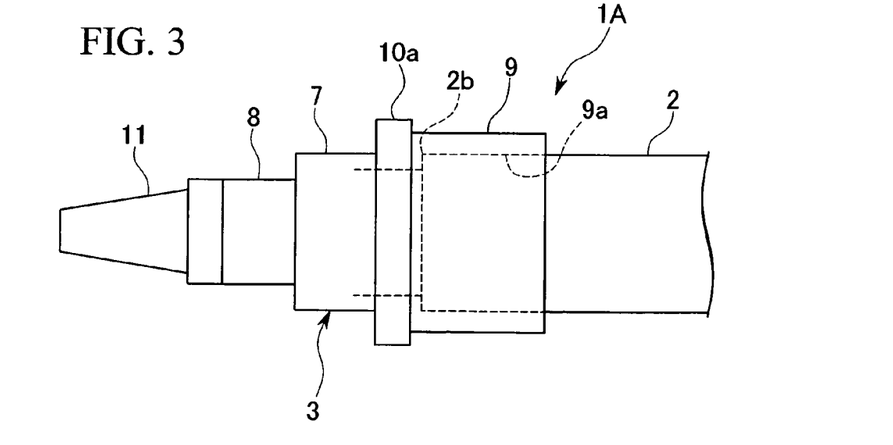
FIG. 3 is a side view of the main part of a combined container-syringe according to the second embodiment of the present invention.
Figure 4:
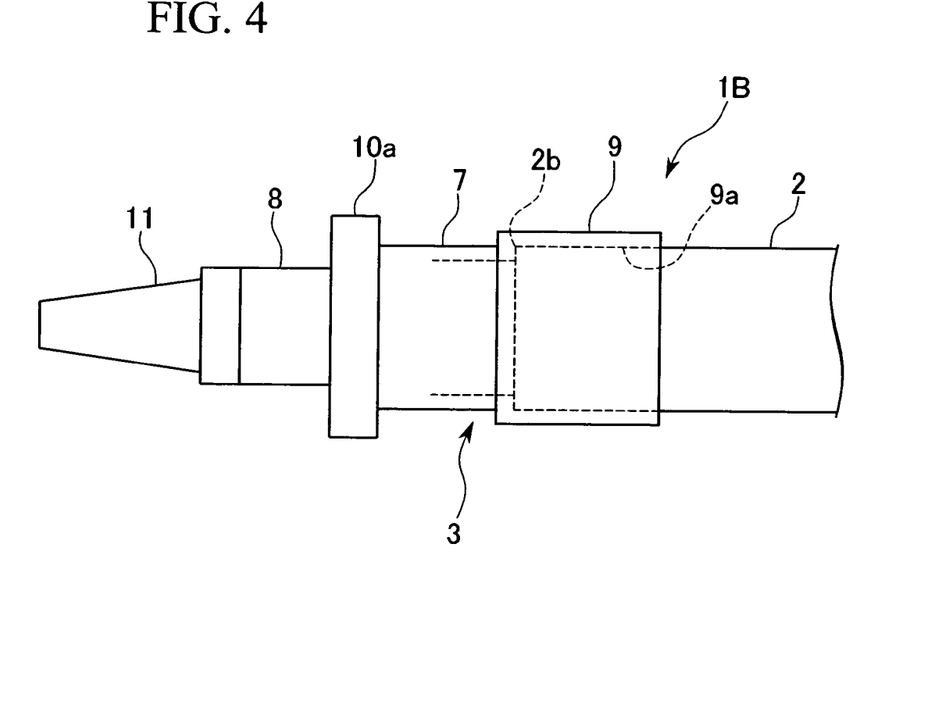
FIG. 4 is a side view of a combined container-syringe according to the third embodiment of the present invention.

In FIGS. 3 and 4, since the parts in common with the combined container-syringe 1 have the same symbols, explanation about these symbols is omitted. Both combined container-syringe 1A and 1B according to the second and third embodiments of the present invention have the same effects as the combined container-syringe 1 according to the first embodiment of the present invention, respectively.

Figure 5:
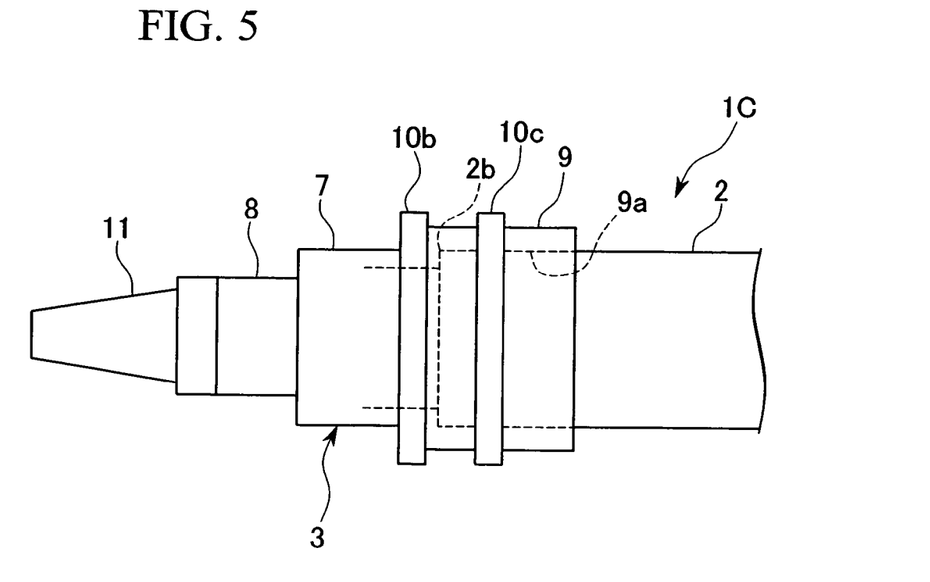
FIG. 5 is a side view of a combined container-syringe according to the fourth embodiment of the present invention.
Figure 6:
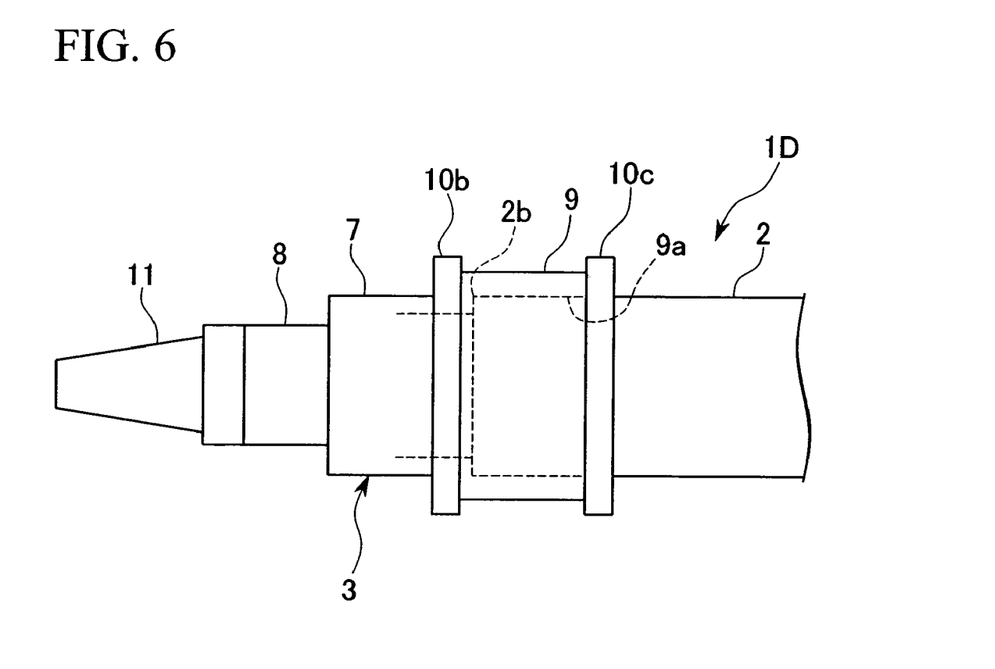
FIG. 6 is a side view of a combined container-syringe according to the fifth embodiment of the present invention.
Figure 7:
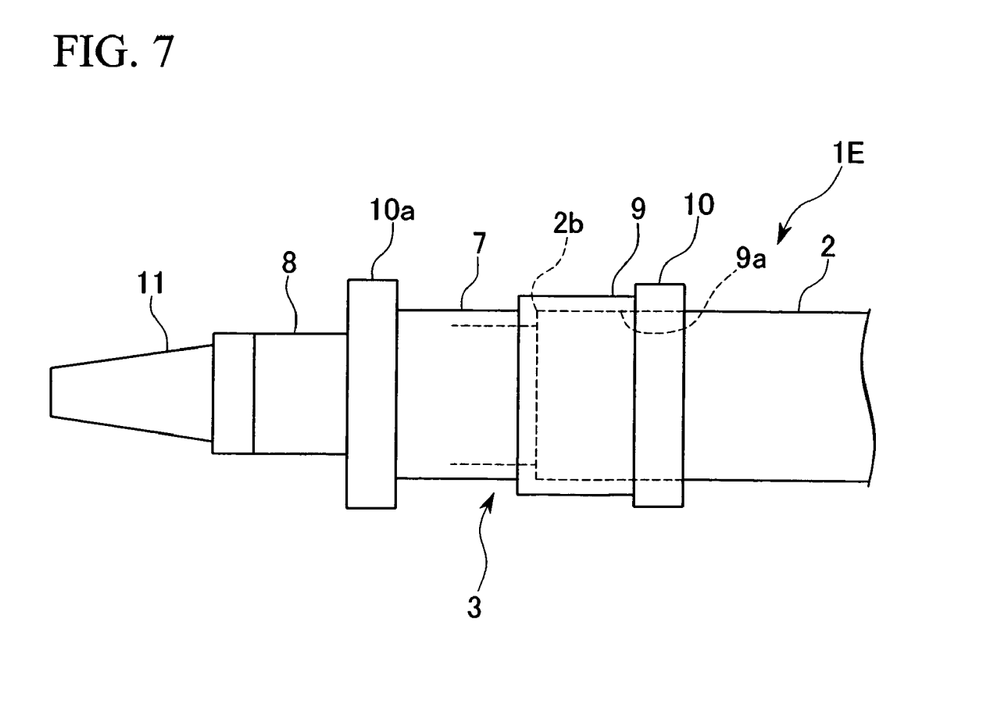
FIG. 7 is a side view of a combined container-syringe according to the sixth embodiment of the present invention.

As shown in FIGS. 5 and 6, a pair of circular ribs 10b, 10c (impact absorption parts) having the same height as the aforementioned circular rib 10 and extending along the direction perpendicular to the axis of the glass cylinder 2 may be provided at the anterior end and middle portion of the fitting part 9 (a combined container-syringe 1C according to the forth embodiment of the present invention shown in FIG. 5), or the circular ribs 10b, 10c may be provided at the anterior end and the posterior end of the aforementioned fitting part 9 (a combined container-syringe 1D according to the fifth embodiment of the present invention shown in FIG. 6). Furthermore, circular ribs 10 and 10a may be provided respectively at the posterior end of the fitting part 9 and at the exterior end of the cylindrical part 7 (a combined container-syringe 1E according to the sixth embodiment of the present invention), for example. The combined container-syringes 1C, 1D and 1E according to these embodiments of the present invention have the same effects as the combined container-syringes 1, 1A and 1B according to the first to the third embodiments of the present invention.

Furthermore, three or more circular ribs may be provided at the fitting part 9 of the cylindrical tip 3, and the ribs which extending along the axial direction of the glass cylinder 2 may be provided on the cylindrical tip 3 at the predetermined intervals along the circumferential direction of the glass cylinder 2, in addition to the ribs extending along the direction perpendicular to the axis of the glass cylinder 2. In addition, the ribs may be provided at the fitting part 9 by providing the ribs inclined toward the axial direction of the glass cylinder 2 and cross over each other in addition to the ribs provided at anterior and posterior ends of the fitting part 9.

Figure 8:
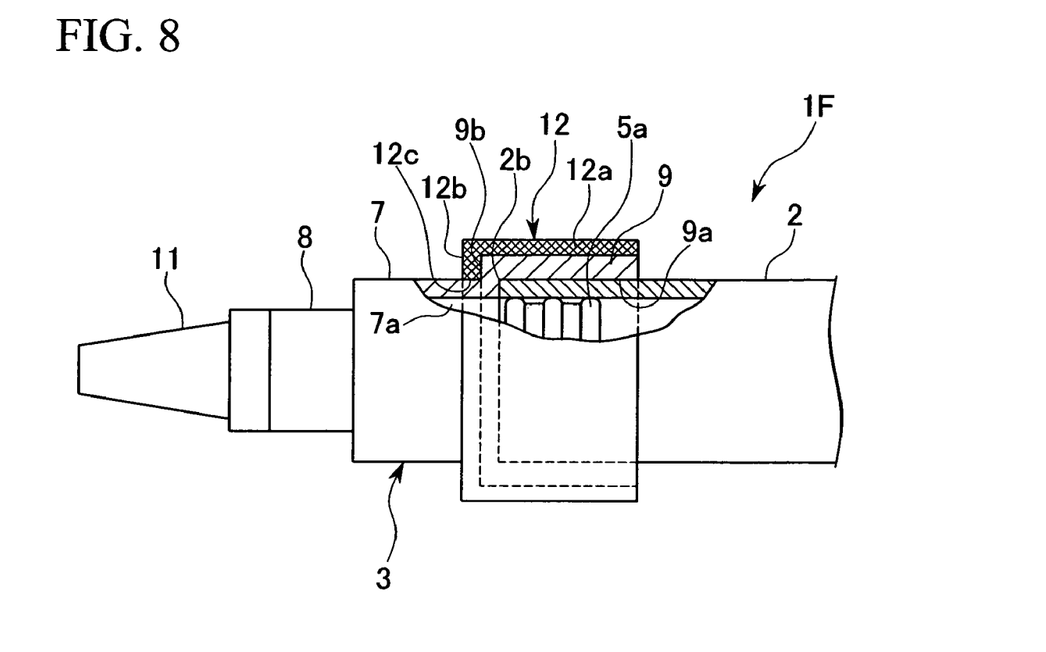
FIG. 8 is a side view of the main part of a combined container-syringe according to the seventh embodiment of the present invention with a partial cross section thereof.

FIG. 8 shows a combined container-syringe 1F according to the seventh embodiment of the present invention. In this syringe 1F, instead of ribs 10, 10a, 10b integrally formed with the fitting part 9 or the cylinder part 7 as shown in the combined container-syringes 1 to 1E according to the first to the sixth embodiments of the present invention, a cylindrical cover 12 (impact absorption part) having impact absorption ability is provided around the exterior surface of the fitting part 9 of the cylindrical tip 3. Since all of other constructions of this syringe 1F are the same as those of the combined container-syringes 1 to 1C according to the first to the fourth embodiments of the present invention, the same symbols are used for the same parts and explanation about these symbols is omitted. The aforementioned cylindrical cover 12 made by a transparent and flexible plastics such as flexible polyvinyl chloride, polyethylene, polypropylene and the like and/or a material such as rubber and the like, and is composed as an integrally molding part of a cylindrical body 12a having 0.5 mm to 3.0 mm of thickness and a circular flange 12b projecting inward from an anterior end portion (leftmost portion in FIG. 8) of the cylindrical body 12a. The cylindrical cover 12 is attached to the fitting 9 from an anterior side of the cylindrical tip 3 and closely covers the exterior surface of the fitting part 9 by inserting the cylindrical tip 3 into the cylinder cover 12 from rearward until an inner plane of the flange 12b attaches an outer step 9b of the fitting part 9. Under this condition, an inner hole 12c of the circular flange 12b is tightly fitted to the outer peripheral surface of the cylindrical part 7 of the cylindrical tip 3. According to the combined container-syringe 1F, even if a larger impactive stress is applied to the fitting part 9 of the cylindrical tip 3 by dropping a combined container-syringe 1F, the cylindrical cover 12 having flexibility and impact absorption ability absorbs and reduces the impact, and prevents a stress to be induced by a larger impactive stress. Therefore, the anterior end 2b of the glass cylinder 2 is reliably prevented from being cracked.

Also, since the cylindrical cover 12 can be attached to the fitting part 9 of the cylindrical tip 3 after assembling conventional syringes, and/or pre-filled the drug into the glass cylinder 2, there is no need for structural change of the cylindrical tip 3 nor need for change of manufacturing or assembling process for conventional combined container-syringes. Therefore, it is easy to manufacture the combined container-syringes having high anti-impact properties. The cylindrical cover 12 may be provided by binding a sheet or tape like material made of flexible plastics or rubber and the like around the outer peripheral surface of the fitting part 9, instead of being made of the molded part to attach firmly around the outer peripheral surface of the fitting part 9 as described above. In this case, the functional effects as same as the cylindrical cover 12 made of the molding part can be expected.

Figure 9:
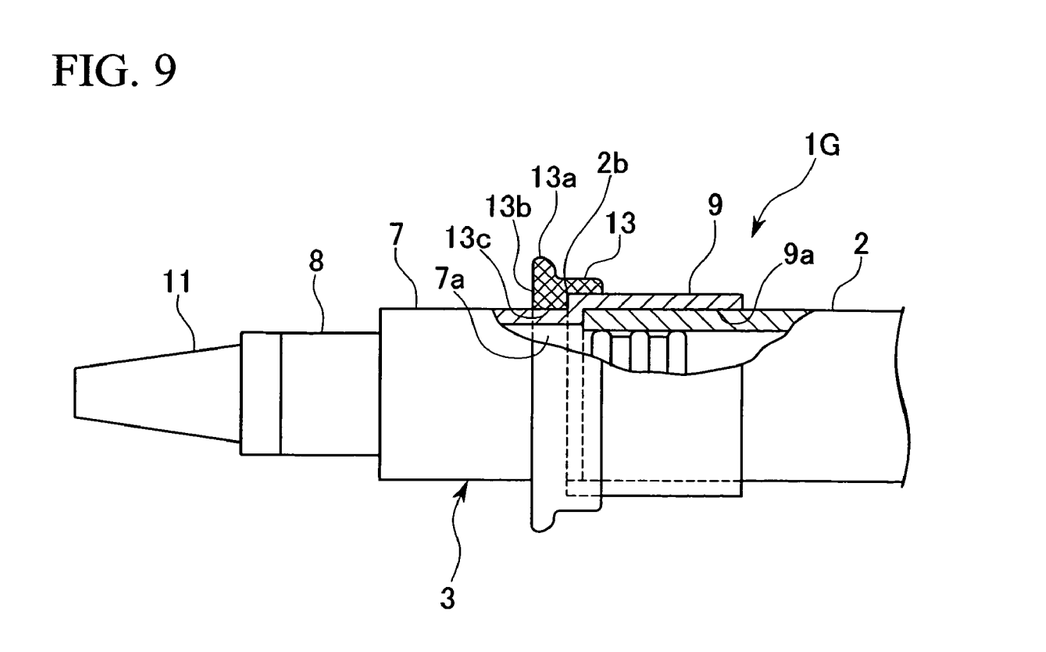
FIG. 9 is a side view of the main part of a combined container-syringe according to the eighth embodiment of the present invention with a partial cross section thereof.

The above mentioned cylindrical cover 12 fully covers the fitting part 9 along the axial direction of the fitting part 9, however, as shown in FIG. 9, a short cylindrical cover 13 (impact absorption part) made of the same material as the cylindrical cover 12 and equipped with a circular rib 13a projecting outward at its anterior end may be attached onto the outer peripheral surface of the anterior end of the fitting part 9 by fitting. Furthermore, an aperture 13c of the circular flange 13b is tightly fitted to the outer peripheral surface of the cylindrical part 7 (a combined container-syringe 1G according to the eighth embodiment of the present invention). The circular rib 13a may be provided at the posterior end of the short cylindrical cover 13 instead of the anterior end of the short cylindrical tip 13, or may be omitted. In the combined container-syringe 10, the functional effects as same as the combined container-syringe 1F in accordance with the combined container-syringe according to the seventh embodiment of the present invention can be expected.

Figure 10:
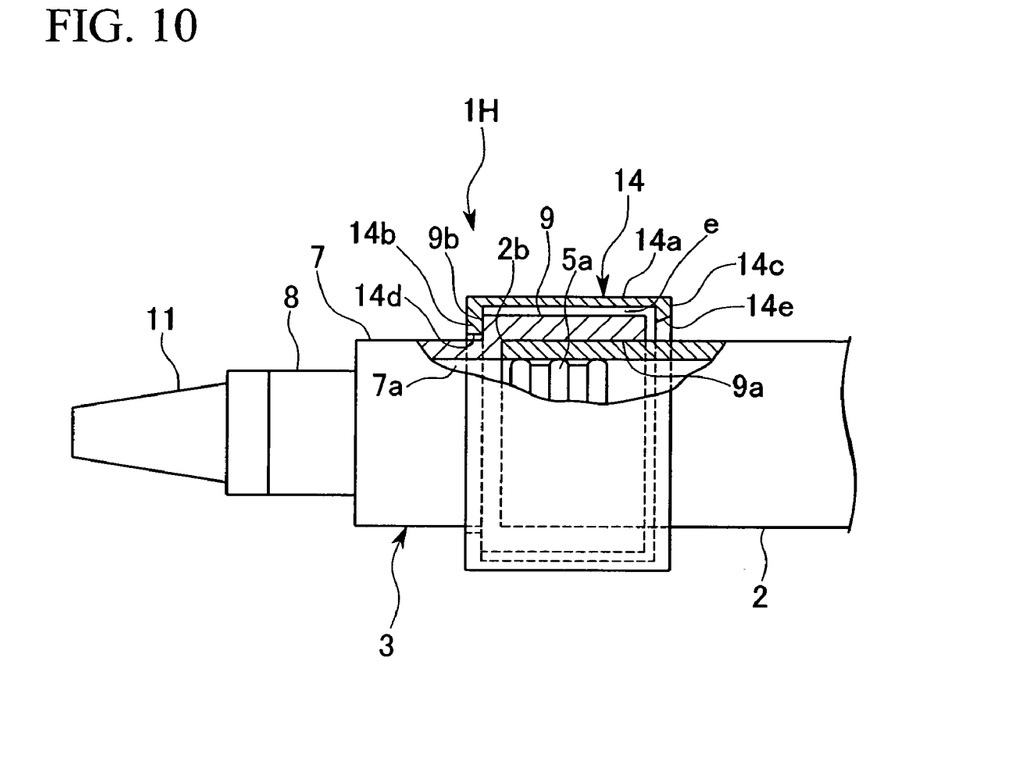
FIG. 10 is a side view of the main part of a combined container-syringe according to the ninth embodiment of the present invention with a partial cross section thereof.

FIG. 10 shows a combined container-syringe 1H according to the ninth embodiment of the present invention. In the combined container-syringe 1H, instead of the cylindrical cover 12 of the combined container-syringe 1F according to the seventh embodiment of the present invention, a cylindrical cover 14 (impact absorption part) made of a rigid plastics is provided on the outer peripheral surface of the fitting part 9 of the cylindrical tip 3 with a clearance e. Since all of other constructions of this syringe 1H are the same as those of the combined container-syringe 1F according to the seventh embodiment of the present invention, the same symbols are used for the same parts and explanation about these symbols is omitted.

The cylindrical cover 14 made of rigid plastics such as polycarbonate, polyester, acrylic resin and the like, is integrally formed with a cylindrical body 14a having 0.5 mm to 3.0 mm of wall thickness and a circular flange 14b and 14c projecting inward from anterior and posterior end portions of the cylindrical body 14a so as to position outside of both ends surfaces of the fitting part 9 of the cylindrical tip 3. The size of the cylindrical body 14a is selected in accordance with the diameter of the glass cylinder 2, however, the inner diameter of the cylindrical body 14a is 0.1 mm to 2.0 mm greater than the outer diameter of the fitting part 9 so as to provide a preferable clearance e between the inner surface of the cylindrical body 14a and the outer surface of the fitting part 9. The circular flange 14b positioned at the anterior end of the cylindrical body 14a defines an aperture 14d so that its inner diameter is identical in the axial direction and can fit loosely around the cylindrical part 7 of the cylindrical tip 3 and the other circular flange 14c positioned at the posterior end of the cylindrical body 14a defines an aperture 14e. This aperture 14e has an inclined (tapered) inner surface so that the inner diameter of its anterior end (leftmost in FIG. 10) is smaller than the outer diameter of the fitting part 9 and is greater than the outer diameter of the cylindrical part 7, and the inner diameter of its posterior end (rightmost in FIG. 10) is greater than that of the fitting part 9. In this embodiment, the inner surface has an inclined plane, however, the shape of the inner surface is not limited to this, and can be a curved (convex or concaved) surface.

In the case of fitting the cylindrical cover 14 to the fitting part 9, by inserting the anterior end of the cylindrical tip 3 into the aperture 14e of the circular flange 14c from the anterior end of the cylindrical tip 3, the aperture 14e is expanded outwardly by the outer step 9b of the fitting part 9 which moves forward so as to push the inclined plane outwardly. Then, the fitting part 9 passes over the cylindrical body 14a, and the aperture 14e is reduced so as to place the fitting part 9 between the flanges 14b and 14c, and the exterior of the fitting part 9 is covered by the cylindrical cover 14. In this condition, since the movement of the cylindrical cover 14 along the axial direction of the glass cylinder 2 is restricted since the inner surfaces of the flanges 14b and 14c interfere the movement of the end surfaces of the fitting part 9. Furthermore, the cylindrical cover 14 can deform or move along a diametral direction of the glass cylinder 2 within the range of the above mentioned clearance e.

Figure 11:
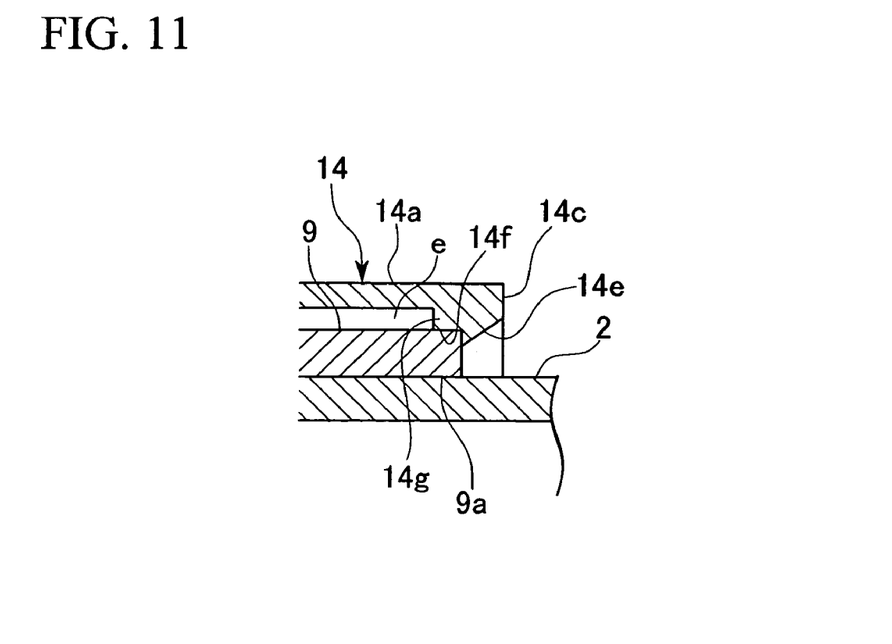
FIG. 11 is an enlarged cross-sectional view of one of variations of the ninth embodiment of the present invention.

In addition, as shown in FIG. 11, if a fitting portion 14g having an aperture 14f for engaging with the posterior end of the fitting part 9, is provided in the inner part of the flange 14c (left part in FIG. 11) of the cylindrical cover 14, the cylindrical cover 14 can reliably be supported by the flange 14b and aperture 14f of the cylindrical cover 14 in a stable condition toward the outer periphery of the fitting part 9 with maintaining the clearance e.

According to the combined container-syringe 1H, when the combined container-syringe 1H is dropped, the cylindrical cover 14 covering the fitting part 9 of the cylindrical tip 3 with the clearance e absorbs the impact by deforming itself so as to prevent the impact being transmitted to the anterior end 2b of the glass cylinder 2 from being cracked reliably. The cylindrical cover 14 can be engaged easily with the fitting part 9 of the cylindrical tip 3 through the aperture 14e having the tapered surface, and the cylindrical cover 14 is reliably be supported to the fitting part 9 of the cylindrical tip 3 by the circular flanges 14b and 14c.

Furthermore, in the above mentioned combined container-syringes 1F and 1G according to the seventh and eighth embodiments of the present invention, the cylindrical cover 14 can be attached to the fitting part 9 of the cylindrical tip 3 of conventional syringes after assembled and/or pre-filled the drug into the glass cylinder 2 as same as the above mentioned combined container-syringes 1F and 1G according to the seventh and eighth embodiments of the present invention, and therefore, there is no need for structural change of the cylindrical tip 3 nor need for change of the manufacturing nor assembling process for the conventional combined container-syringe. Accordingly, it is easy to manufacture the combined container-syringe having high anti-impact properties.

In this embodiment, if the difference between the inner diameter of the cylindrical body 14a of the cylindrical cover 14 and the outer diameter of the fitting part 9 of the cylindrical tip 3 is less than 0.5 mm to 1.0 mm, the above mentioned impact absorption effect is decreased and it cannot be expected to effectively prevent the anterior end 2b of the glass cylinder 2 from being cracked, and if the difference is more than 0.5 mm to 1.0 mm, the shape of the cylindrical tip 3 becomes rather unnaturally larger and causes inconvenient handling of the combined container-syringe inconvenient.

Although this invention has been explained by using the examples of the combined container-syringes 1 to 1E for pre-filling one kind of drug between the front and end stoppers 5a and 5b in the glass cylinder 2, this invention is not limited to the examples but is also applicable to a multiple chamber combined container-syringe with more than two spaces separated by middle stoppers between the front stopper and the end stopper and pre-filled with more than one of drugs in the glass cylinder 2.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A combined container-syringe comprising:
a glass cylinder in which a drug is pre-filled and sealed therein by stoppers, a cylindrical tip provided at an exterior portion of an anterior end of said glass cylinder, and
a finger grip provided at an exterior portion of a posterior end part of said glass cylinder, wherein
said cylindrical tip is composed of a cylindrical part and a cylindrical fitting part which is integrally formed at the posterior end of said cylindrical part with an outer diameter greater than that of said cylindrical part,
said cylindrical tip is connected to said glass cylinder by fitting an inner hole of said fitting part around an outer surface of the anterior end part of said glass cylinder, and
an impact absorption part is provided around the exterior portion of said cylindrical tip and a diameter of said impact absorption part is greater than an outer diameter of said fitting part, and wherein
said impact absorption part is a circular rib formed integrally with said fitting part along a direction perpendicular to an axis of said glass cylinder on a posterior end of said fitting part.

2. A combined container-syringe comprising:
a glass cylinder in which a drug is pre-filled and sealed therein by stoppers;
a cylindrical tip provided at an exterior portion of an anterior end part of said glass cylinder; and
a finger grip provided at an exterior portion of a posterior end of said glass cylinder, wherein
said cylindrical tip is composed of a cylindrical part and a cylindrical fitting part which is integrally formed at the posterior end of said cylindrical part with an outer diameter greater than that of said cylindrical part, said cylindrical tip is connected to said glass cylinder by fitting an inner hole of said fitting part around an outer surface of the anterior end part of said glass cylinder, and
two impact absorption parts are provided around the exterior portion of said cylindrical tip and a diameter of said impact absorption part is greater than an outer diameter of said fitting part, and wherein
said impact absorption parts are circular ribs formed integrally with said fitting part along a direction perpendicular to an axis of said glass cylinder on an anterior end and a posterior end of said fitting part separately.

3. A combined container-syringe comprising:
a glass cylinder in which a drug is pre-filled and sealed therein by stoppers, a cylindrical tip provided at an exterior portion of an anterior end part of said glass cylinder, and a finger grip provided at an exterior portion of a posterior end of said glass cylinder, wherein said cylindrical tip is composed of a cylindrical part and a cylindrical fitting part which is integrally formed at the posterior end of said cylindrical part with an outer diameter greater than that of said cylindrical part, said cylindrical tip is connected to said glass cylinder by fitting an inner hole of said fitting part around an outer surface of the anterior end part of said glass cylinder, and an impact absorption part is provided around the exterior portion of said cylindrical tip and a diameter of said impact absorption part is greater than an outer diameter of said fitting part, wherein said impact absorption part is a cylindrical cover made of plastics having flexibility and shock absorption ability and attached to said fitting part at a posterior end of said fitting part.

4. A combined container-syringe comprising:

a glass cylinder in which a drug is pre-filled and sealed therein by stoppers, a cylindrical tip provided at an exterior portion of an anterior end part of said glass cylinder, and a finger grip provided at an exterior portion of a posterior end of said glass cylinder, wherein said cylindrical tip is composed of a cylindrical part and a cylindrical fitting part which is integrally formed at the posterior end of said cylindrical part with an outer diameter greater than that of said cylindrical part, said cylindrical tip is connected to said glass cylinder by fitting an inner hole of said fitting part around an outer surface of the anterior end part of said glass cylinder, and an impact absorption part is provided around the exterior portion of said cylindrical tip and a diameter of said impact absorption part is greater than an outer diameter of said fitting part, and wherein said impact absorption part is a cylindrical cover which is made of rigid plastics and placed around the outer surface of a posterior end of said fitting part with a predetermined clearance.

5. A combined container-syringe according to claim 4, wherein said cylindrical cover has first and second circular flanges which project inwardly at two end portions of said fitting part;

wherein said first flange defines an aperture the inner surface of which can be fitted around an outer surface of a cylindrical part of said cylindrical tip;

said second flange has a tapered insertion hole; and said tapered insertion hole has a diameter less than that of the outer surface of said fitting part at one side of said second flange, and greater than the outer surface of said fitting part at the other side of said second flange.

* * * * *